(12) United States Patent
Hersbach

(10) Patent No.: US 8,553,901 B2
(45) Date of Patent: Oct. 8, 2013

(54) CANCELLATION OF BONE-CONDUCTED SOUND IN A HEARING PROSTHESIS

(75) Inventor: Adam Hersbach, Richmond (AU)

(73) Assignee: Cochlear Limited, Macquarie University, NSW (AU)

( * ) Notice: Subject to any disclaimer, the term of this patent is extended or adjusted under 35 U.S.C. 154(b) by 444 days.

(21) Appl. No.: 12/867,240

(22) PCT Filed: Feb. 11, 2009

(86) PCT No.: PCT/US2009/033828
§ 371 (c)(1), (2), (4) Date: Aug. 11, 2010

(87) PCT Pub. No.: WO2009/102811
PCT Pub. Date: Aug. 20, 2009

(65) Prior Publication Data
US 2010/0310084 A1 Dec. 9, 2010

(51) Int. Cl.
*G10K 11/16* (2006.01)

(52) U.S. Cl.
USPC ............ 381/71.6; 381/313; 381/326; 600/25

(58) Field of Classification Search
USPC ................. 381/326, 317, 313, 71.6; 600/25
See application file for complete search history.

(56) References Cited

U.S. PATENT DOCUMENTS

| | | | | |
|---|---|---|---|---|
| 6,888,949 B1 * | 5/2005 | Vanden Berghe et al. | .... | 381/317 |
| 7,616,771 B2 * | 11/2009 | Lenhardt et al. | ............. | 381/326 |
| 2003/0086581 A1 | 5/2003 | Killion et al. | | |
| 2004/0264721 A1 | 12/2004 | Allegro et al. | | |
| 2005/0157895 A1 | 7/2005 | Lichblau | | |
| 2005/0222487 A1 * | 10/2005 | Miller et al. | .................... | 600/25 |
| 2006/0155346 A1 * | 7/2006 | Miller, III | ........................ | 607/57 |
| 2007/0106345 A1 | 5/2007 | Seligman | | |
| 2007/0127753 A1 * | 6/2007 | Feng et al. | .................... | 381/313 |
| 2008/0123866 A1 * | 5/2008 | Rule et al. | .................... | 381/71.6 |

OTHER PUBLICATIONS

International Search Report, PCT/US09/33828, mailed Apr. 15, 2009.
International Preliminary Report on Patentability, PCT/US09/33828, mailed Jan. 21, 2010.

* cited by examiner

*Primary Examiner* — Duc Nguyen
*Assistant Examiner* — Phan Le
(74) *Attorney, Agent, or Firm* — Kilpatrick, Townsend & Stockton, LLP

(57) ABSTRACT

An hearing prosthesis configured to cancel received bone-conducted sound. The hearing prosthesis comprises: first and second matched microphones configured to be implanted in a recipient in a spaced arrangement such that the first microphone receives air-conducted sound signals and bone-conducted sound signals substantially simultaneously, and wherein the second microphone receives bone-conducted sound signals at substantially the same time as the first microphone and receives the air-conducted sound signals after a time delay. The time delay results in a relative phase difference between the air-conducted sound signals and the bone-conducted sound signals received by the second microphone. The prosthesis also comprises a noise cancellation system configured to cancel, based on the phase difference, the bone-conducted sound signals received by the first and second microphones.

20 Claims, 12 Drawing Sheets

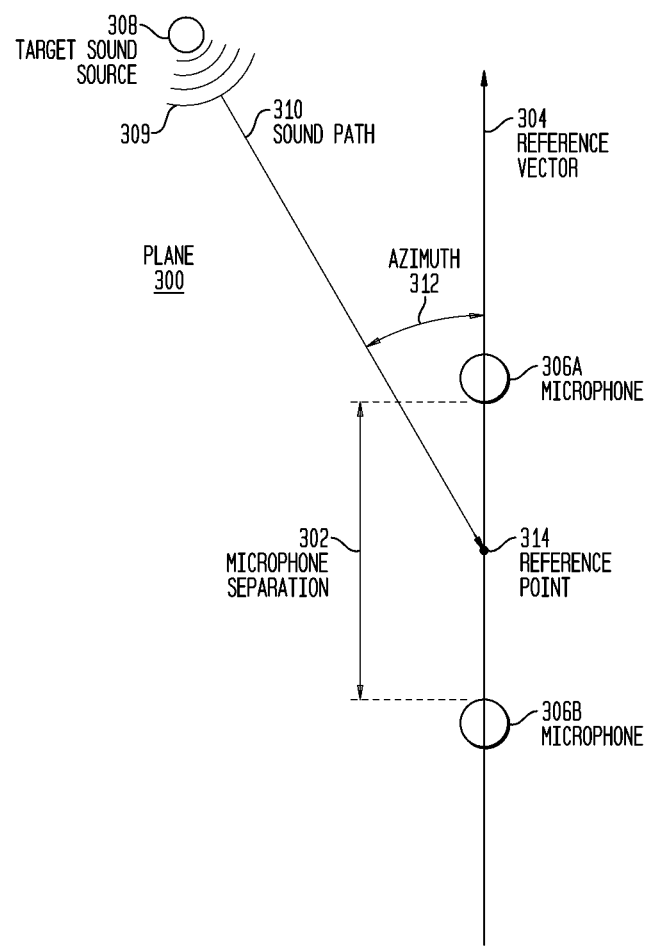

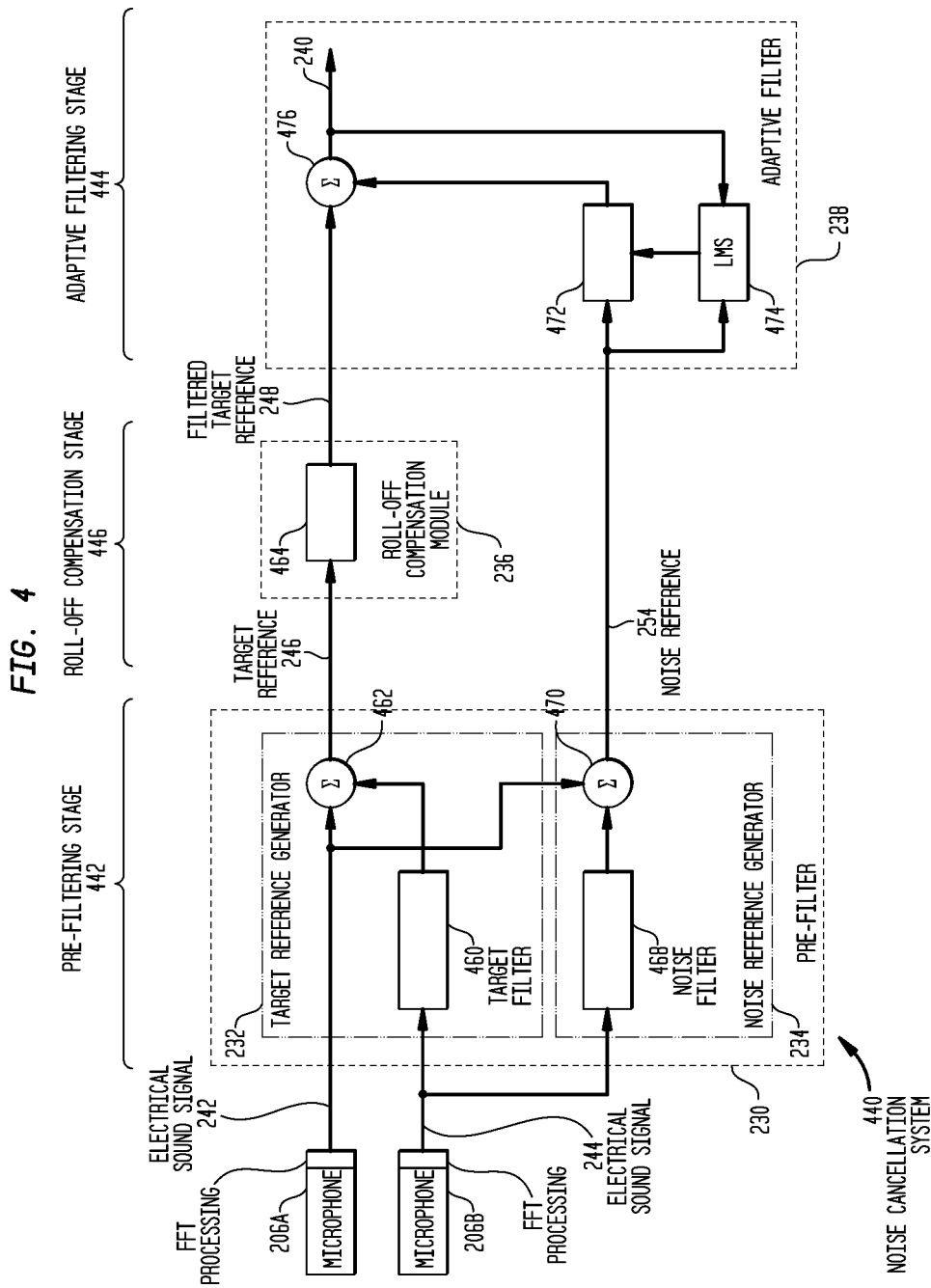

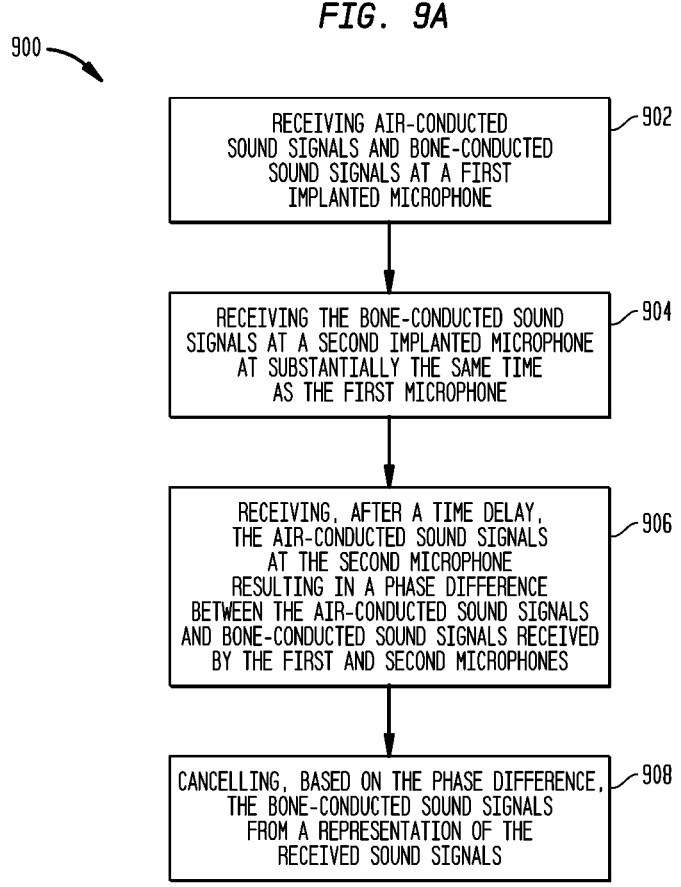

910 — GENERATING BASED ON THE PHASE DIFFERENCE A TARGET REFERENCE SIGNAL PRIMARILY COMPRISING THE AIR-CONDUCTED SOUND SIGNALS AND FROM WHICH THE BONE-CONDUCTED SOUND SIGNALS ARE SUBSTANTIALLY CANCELLED

912 — GENERATING BASED ON THE PHASE DIFFERENCE A NOISE REFERENCE SIGNAL PRIMARILY COMPRISING THE BONE-CONDUCTED SOUND SIGNALS, AND FROM WHICH THE AIR-CONDUCTED SOUND SIGNALS HAVE BEEN SUBSTANTIALLY CANCELLED; AND

914 — ADAPTIVELY FILTERING THE TARGET REFERENCE SIGNAL AND THE NOISE REFERENCE SIGNAL TO FURTHER CANCEL BONE-CONDUCTED SOUND FROM THE TARGET REFERENCE SIGNAL

CANCELLATION OF BONE-CONDUCTED SOUND IN A HEARING PROSTHESIS

CROSS-REFERENCE TO RELATED APPLICATION

The present application is a national stage of International Application No. PCT/U.S.09/033,828, filed Feb. 11, 2009, and claims priority from Australian Patent Application No. 2008900633, filed Feb. 11, 2008. These applications are hereby incorporated by reference herein.

BACKGROUND

1. Field of the Invention

The present invention relates generally to hearing prostheses, and more particularly, to cancellation of bone-conducted sound in a hearing prosthesis.

2. Related Art

Hearing loss, which may be due to many different causes, is generally of two types, conductive and sensorineural. In some cases, a person may have hearing loss of both types. Conductive hearing loss occurs when the normal mechanical pathways that sound travels to the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from sensorineural hearing loss are thus unable to derive suitable benefit from conventional hearing aids. As a result, hearing prostheses that deliver electrical stimulation to nerve cells of a recipient's auditory system have been developed to provide persons having sensorineural hearing loss with the ability to perceive sound. Such stimulating hearing prostheses include, for example, auditory brain stimulators and cochlear prostheses (commonly referred to as cochlear prosthetic devices, cochlear implants, cochlear devices, and the like; simply "cochlear implants" herein.) As used herein, a recipient's auditory system includes all sensory system components used to perceive a sound signal, including hearing sensation receptors, neural pathways, including the auditory nerve and spiral ganglion, and regions of the brain that sense sound.

Most sensorineural hearing loss is due to the absence or destruction of the cochlea hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Conventional cochlear implants have generally included an external assembly directly or indirectly attached to the body of the recipient, and an internal assembly which is implanted in the recipient.

More recently, cochlear implants have been designed such that all of the components of the device are implanted subcutaneously; that is there is no external assembly. Because such cochlear implants are entirely implantable, they are commonly referred to as a "totally" or "fully" implantable cochlear implant. One exemplary totally implantable cochlear implant is described in greater detail in U.S. Pat. No. 7,346,397.

Unlike conventional cochlear implants in which sound input elements, such as a microphone, are positioned external to the recipient, a totally implantable cochlear implant includes a subcutaneously-implanted microphone. An implanted microphone may be sensitive to airborne sound, referred to herein as air-conducted sound, as well as sound conducted to the microphone via the bones of the recipient's skull, referred to herein as bone-conducted sound.

SUMMARY

In one aspect of the present invention, a method for cancelling bone-conducted sound in a hearing prosthesis having first and second matched microphones implanted in a recipient in a spaced arrangement is provided. The method comprises: receiving at the first microphone air-conducted sound signals and bone-conducted sound signals substantially simultaneously; receiving the bone-conducted sound signals at the second microphone at substantially the same time as the first microphone; receiving, after a time delay, the air-conducted sound signals at the second microphone, the time delay resulting in a relative phase difference between the air-conducted sound signals and the bone-conducted sound signals received by the first and second microphones; and cancelling, based on the phase difference, the bone-conducted sound signals from a representation of the sound signals received by the first and second microphones.

In another aspect of the present invention, a hearing prosthesis configured to cancel received bone-conducted sound is provided. The hearing prosthesis comprises: first and second matched microphones configured to be implanted in a recipient in a spaced arrangement such that the first microphone receives air-conducted sound signals and bone-conducted sound signals substantially simultaneously, and wherein the second microphone receives bone-conducted sound signals at substantially the same time as the first microphone and receives the air-conducted sound signals after a time delay, the time delay resulting in a relative phase difference between the air-conducted sound signals and the bone-conducted sound signals received by the first and second microphones; and a noise cancellation system configured to cancel, based on the phase difference, the bone-conducted sound signals from a representation of the sound signals received by the first and second microphones.

BRIEF DESCRIPTION OF THE DRAWINGS

Embodiments of the present invention are described below with reference to the attached drawings, in which:

FIG. 3A is a schematic diagram illustrating the orientation of microphones to a target sound source, in accordance with embodiments of the present invention;

FIG. 4 is a functional block diagram of a noise cancellation system in accordance with embodiments of the present invention;

FIG. 9A is a flowchart illustrating a noise cancellation method in accordance with embodiments of the present invention; and FIG. 9B is a flowchart illustrating the cancellation of bone-conducted noise in accordance with certain embodiments of the method of FIG. 9A.

DETAILED DESCRIPTION

Aspects of the present invention are generally directed to facilitating the processing of air-conducted sound through the reduction and/or elimination of bone-conducted sound. A hearing prosthesis in accordance with embodiments of the present invention comprises at least two matched microphones implanted in a recipient in a spaced arrangement. received bone-conducted sound and body noise. More specifically, the hearing prosthesis includes a noise cancellation system that cancels bone-conducted sound signals, such as body noise, conducted to the microphones via the recipient's skull.

Embodiments of the present invention are described herein primarily in connection with one type of hearing prosthesis, namely a totally implantable cochlear prostheses (commonly referred to as cochlear prosthetic devices, cochlear implants, cochlear devices, and the like; simply "cochlear implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that electrically, acoustically or mechanically stimulate components of the recipient's outer, middle or inner ear.

Figure 1:
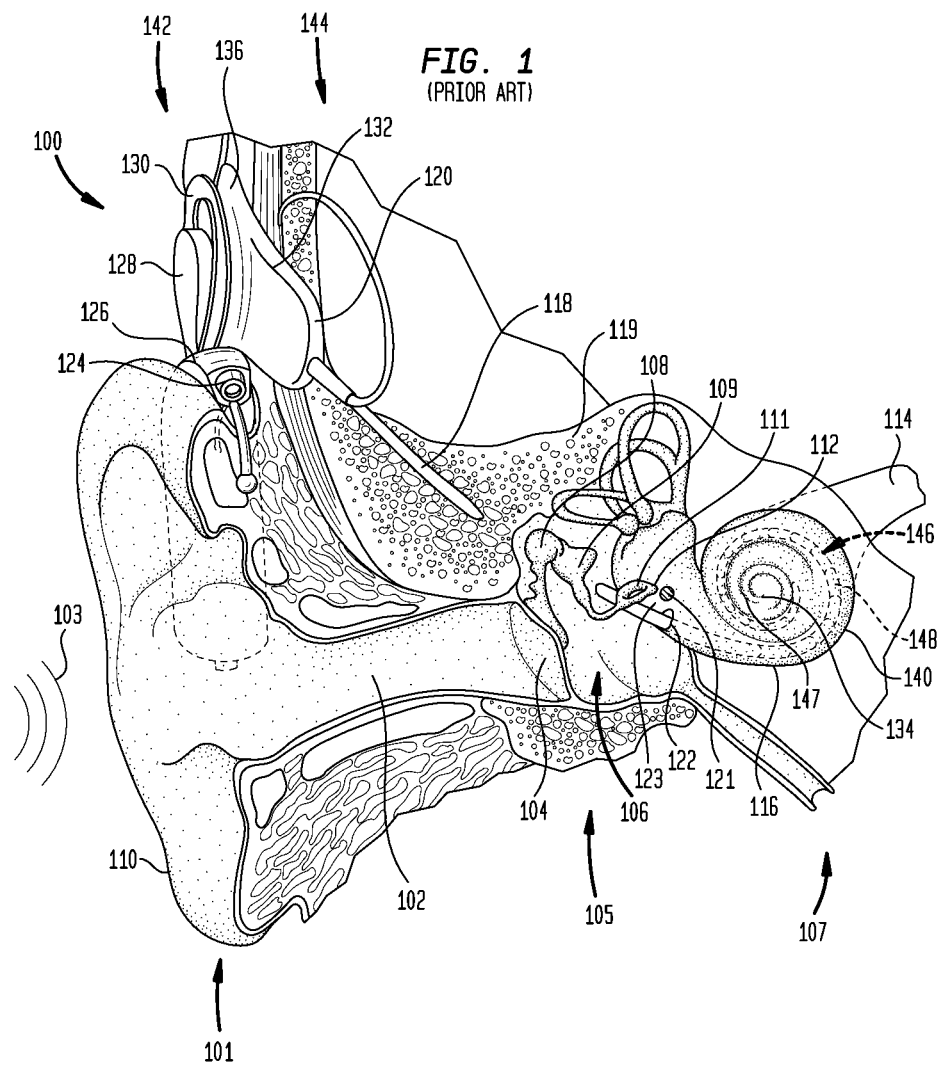
FIG. 1 is a perspective view of a conventional cochlear implant implanted in a recipient.

FIG. 1 is perspective view of a conventional cochlear implant, referred to as cochlear implant 100, implanted in a recipient. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

FIG. 1 illustrates a cochlear implant 100 implanted in the recipient. Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119. Electrode assembly 118 is implanted into cochlea 104. As described below, electrode assembly is implanted in cochlea 140. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes or contacts 148, sometimes referred to as electrode or contact array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Figure 2A:
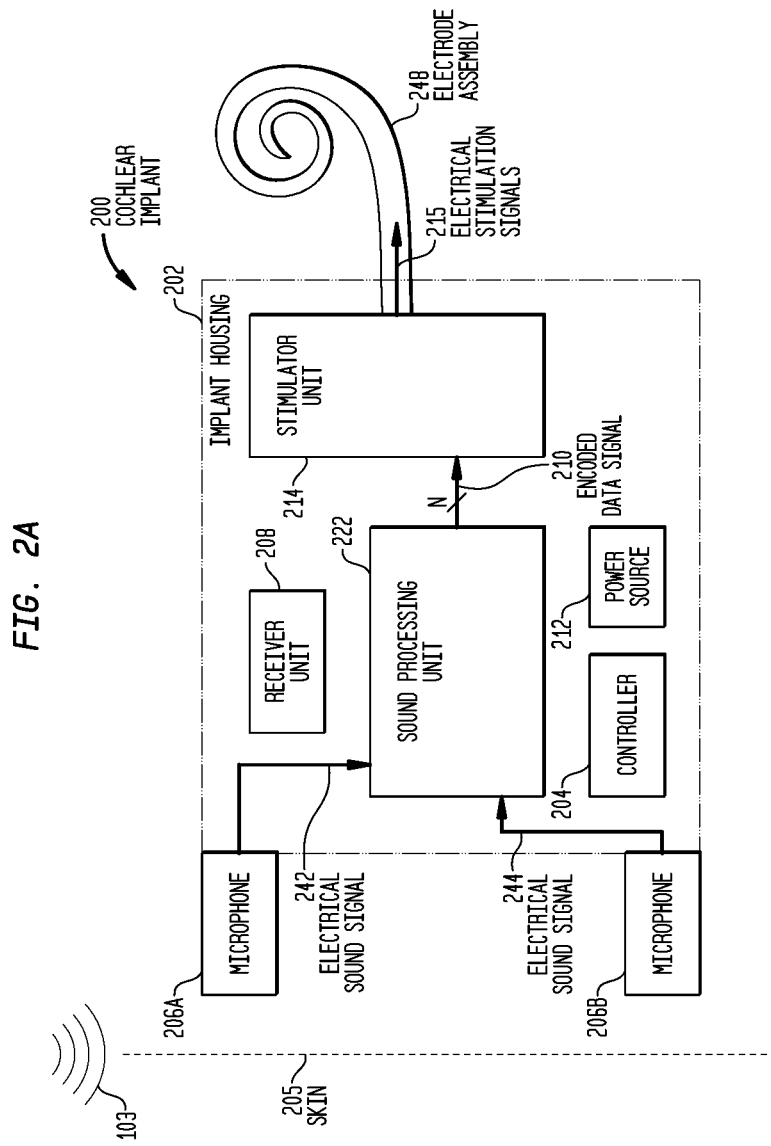
FIG. 2A is a functional block diagram of a cochlear implant in which embodiments of the present invention may be implemented.

FIG. 2A is a functional block diagram of a totally-implantable cochlear implant 200 in which embodiments of the present invention may be implemented. In the illustrative embodiment, cochlear implant 200 is totally or fully implantable; that is, all components of cochlear implant 200 are configured to be implanted under skin 205 of a recipient. As shown, one or more components of cochlear implant 200 may be disposed in a hermetically sealed implant housing 202. Because all components of cochlear implant 200 are configured to be implanted, cochlear implant 200 operates, for at least a period of time, without the need of an external device.

As shown, cochlear implant 200 comprises two sound input elements, shown as microphones 206A and 206B (collectively and generally referred to as microphone or microphones 206), to receive and convert an acoustic sound signal 103 into electrical signals 242, 244. It should be appreciated that embodiments of the present invention may use any implantable microphone, and/or any microphone position, now know or later developed. However, as described in greater detail below, microphones 206 are matched; that is they have substantially similar sensitivities to each of air-conducted sound and bone-conducted sound. In other words, the sensitivity of microphone 206A to each of air-conducted sound and bone-conducted sound is substantially the same as the sensitivity of microphone 206B to each of air-conducted sound and bone-conducted sound.

Cochlear implant 200 further comprises a sound processing unit 222 that implements one or more speech processing and/or coding strategies to convert electrical signals 242, 244 into encoded data signals 210 that are provided to a stimulator unit 214. Based on encoded data signals 210, stimulator unit 214 generates electrical stimulation signals 215 for delivery to the cochlea of the recipient. In the embodiment illustrated in FIG. 2A, cochlear implant 200 comprises an embodiment of electrode assembly 118 of FIG. 1, referred to as electrode assembly 248, for delivering stimulation signal 215 to the cochlea. Details of sound processing unit 222 are provided below.

As shown in FIG. 2A, cochlear implant 200 further comprises a receiver unit 208 configured to communicate with systems or components positioned externally to the recipient, such as a fitting system (not shown), charging station (also not shown), etc. Also included in cochlear implant 200 is a power source 212 that provides power to the components of cochlear implant 200. Power source 212 may comprise, for example, a rechargeable battery. Cochlear implant 200 further comprises controller 204. Controller 204 may include various components for controlling the operation of cochlear implant 200, or for controlling specific components of cochlear implant 200. For example, controller 204 may control the delivery of power from power source 212 to other components of cochlear implant 200.

As noted above, an implanted microphone may be sensitive to both air-conducted sound (sometimes referred to as air-conducted sound signals herein) as well as bone-conducted sound (sometimes referred to as bone-conducted sound signals herein). However, in a typical implanted system, only the air-conducted sound is useful in evaluating a target acoustic sound signal. The bone-conducted sounds typically comprises noise that degrades performance of the microphone. For example, body borne sound, such as breathing, may be conducted through the recipient's skull to an implanted microphone. The resulting bone-conducted sound detected by the microphone may have an amplitude which is the same, or greater than the amplitude of a concurrently-received air-conducted sound. In such situations, the implanted microphone detects both the desired air-conducted sound as well as the bone-conducted noise, and the hearing prosthesis is unable to differentiate between the sounds.

Figure 2B:
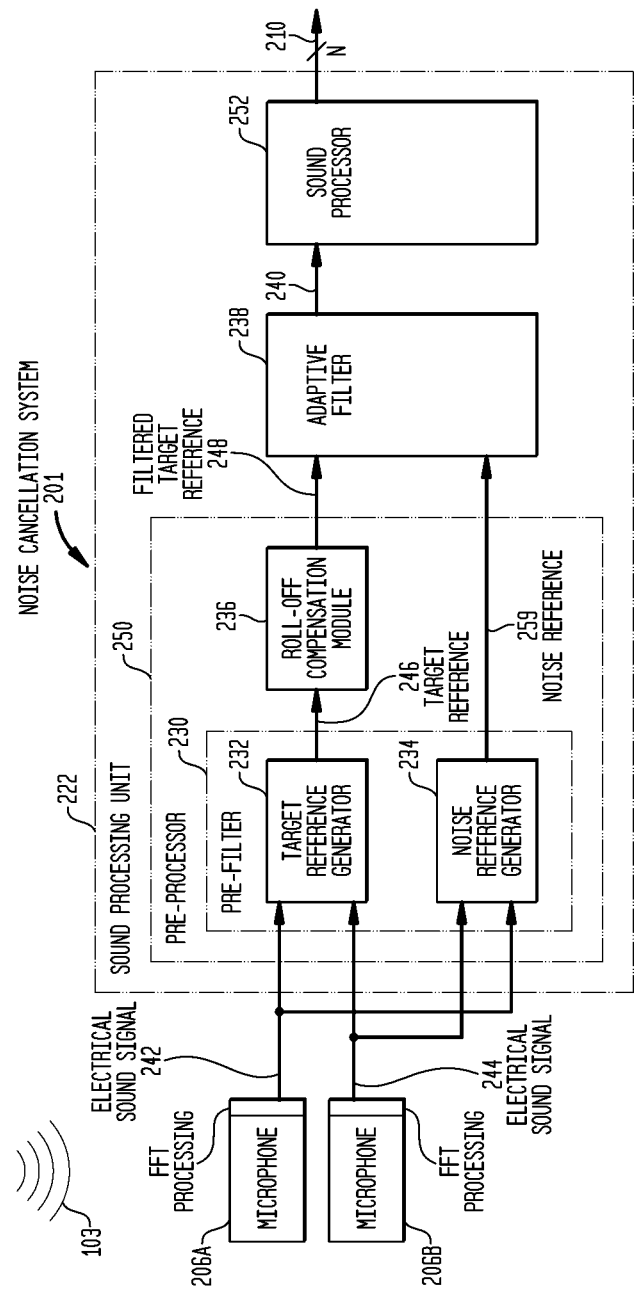
FIG. 2B is a functional block diagram of the sound processing unit illustrated in FIG. 2A configured to implement embodiments of the present invention.

FIG. 2B is a functional block diagram illustrating an exemplary arrangement of sound processing unit 222 configured to eliminate or substantially reduce degradation resulting from bone-conducted noise detected by implanted microphones. More particularly, as detailed below, sound processing unit 222 comprises a noise cancellation system 201 configured to substantially reduce or eliminate bone-conducted sound signals, such as body noise, conducted to implanted microphones 206.

As shown in FIG. 2B, sound processing unit 222 comprises a pre-processor 250, an adaptive filter 238 and a sound processor 252. Pre-processor 250 comprises a pre-filter 230 and a roll-off compensation module 236. As noted above, acoustic sound signals 103 are received by microphones 206A, 206B and converted to electrical signals 242, 244 respectively. Microphones 206 implement processing in which a Fast Fourier Transform (FFT) is used to convert the detected signals to the frequency domain, shown as in FIG. 2B as FFT processing in microphones 206. Thus, electrical signals 242, 244 output by microphones 206 are frequency domain signals.

As detailed below with reference to FIGS. 3A-3B, sound originates from a target sound source positioned at a target location. Microphones 206 are positioned such that there is a difference in the acoustic path distance for sounds received by the two microphones. In the illustrative embodiment, microphone 206A is closer to the source of target acoustic sound signals 103, thereby creating a time delay between when signals are received at microphones 206A and 206B. As detailed below, this time delay is used by noise cancellation system 201 of the present invention to eliminate bone-conducted noise from a representation of the received sound signals.

Returning to FIG. 2B, electrical signals 242 and 244 are both provided to target reference generator 232 in pre-filter 230. Target reference generator 232 is configured to output a target reference signal 246 which primarily comprises components of a target acoustic signal, and from which predominate noise components (such as bone-conducted sounds) have been removed. Details of the operation of target reference generator 232 and the corresponding portions of the noise cancellation system are described in greater detail below with reference to FIG. 4.

Target reference signal 246 is provided to a roll-off compensation module 236. Roll-off compensation module 236 is configured to ensure that the frequency shape of target reference signal 246 is the same as, or substantially similar to, the frequency shape of an unfiltered acoustic signal originating from the direction of the target source. Details of the operation of roll-off compensation module 236 and the corresponding portions of the noise cancellation system are described in greater detail below with reference to FIG. 4.

As noted above, both electrical signals 242, 244 are provided to target reference generator 232. The signals are also both provided to noise reference generator 234. Noise reference generator 234 is configured to output a noise reference signal 254 which primarily comprises noise components, and from which the target acoustic signal has been substantially removed. Details of the operation of noise reference generator 234 and the corresponding portions of the noise cancellation system are described in greater detail below with reference to FIG. 4.

FIG. 3A is a schematic diagram illustrating the positional relationship between matched implanted microphones 306A, 306B and a target sound source 308. Target sound source 308 generates a sound 309 that impinges upon microphones 306. Sound 309 generated by target sound source 308 travels on a path 310 toward a reference point 314 spaced between microphones 306A, 306B. Microphones 306 are located in an imaginary plane 300, and are separated by a straight line distance 302 in plane 300. The relative position of target sound source 308 and microphones 306 is such that the sound 309 emitted by the target impinges on the microphones at different times.

The relative position of a target sound source 308 and microphones 306 is expressed in terms an azimuth 312 relative to a reference vector 304. Reference vector 304 resides in plane 300 and intersects both microphones 306. Similarly, azimuth 312 also resides in plane 300. Therefore, azimuth 312 is the angular offset between sound path 310 and reference vector 304.

Because microphone 306A is positioned a distance 302 closer to target source 308 than microphone 306B, sound signal 309 emitted by target source 308 will be received by microphone 306A prior to source signal 309 being received by microphone 306B. In other words, there is a time delay between when source signal 309 arrives at each of the microphones 306. The path difference for sound is defined by the vector component of sound signal 309 which is parallel with reference vector 304.

The time delay is greatest when target sound source 308 is located along reference vector 304; that is, when azimuth 312 is zero. It should be appreciated, however, that embodiments of the present invention may be implemented with any relative position that results in the noted time delay.

Figure 3B:
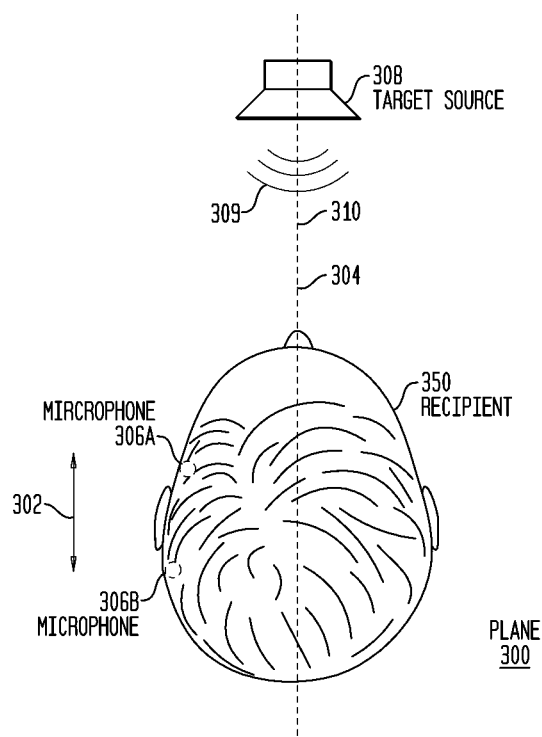
FIG. 3B is a schematic diagram illustrating exemplary microphone locations in accordance with embodiments of the present invention.

FIG. 3B is schematic top view of a recipient's head 350 illustrating one exemplary configuration of matched implanted microphones 306A, 306B. Matched microphones 306 are implanted under skin 205 (FIG. 2A) of recipient 350 and reside in a horizontal plane 300. As shown, microphones are spaced apart by a distance 302 and, as such, are referred to herein as being implanted in a spaced arrangement. The recipient is facing target sound source 308. When target sound source 308 is greater than approximately 30 cm from the recipient, the target may be laterally offset from reference vector 304 with substantially no change in performance due to the target being in the far field. As such, in this example in which the recipient is facing target source 308, reference vector 304 is also laterally offset from microphones 306 to emphasize the target source 308 being at a zero azimuth 312 from the microphones. In other words, when the target source position is directly in front of the recipient, reference vector 304 and sound path 310 are coincident as shown in FIG. 3B.

In the exemplary arrangement of FIG. 3B, microphone 306A is positioned a horizontal distance 302 closer to target signal source 308 than microphone 306B. Due to this horizontal spacing of microphones 306, an acoustic signal 309 output by target source 308 will first arrive at the foremost microphone 306A and then, after a small time delay, will arrive at rear microphone 306B. The effective path distance 302 between the two microphones 306 creates, for air-conducted sound 309, a phase difference in the response between the two microphones to the received sound signals; that is, there is a relative phase difference between the sound signals received by microphone 306A and 306B. On the other hand, due to the high speed of sound conduction through bone, bone-conducted sound is presumed to arrive at the two microphones 306 with an effective path distance that is very close to zero and therefore in phase.

It is this difference in the relative phase between air-conducted sound and bone-conducted sound received by microphones 306 that is exploited with adaptive filtering to remove the bone-conducted sound while maintaining sufficient sensitivity to the air-conducted sound. In other words, the difference in the phase difference generated by air-conducted and bone-conducted sound is utilized in embodiments of the present invention to cancel the bone-conducted sound. It is for this reason that the two microphones have similar characteristics in terms of the air conducted and bone-conducted response; that is they are matched. The illustrative position of target signal source 308 directly in front of recipient is not only a common scenario, but also maximizes the time delay between when the microphones receive sound emitted from the target since sound path 310 is coincident with reference vector 304.

It should be appreciated that microphones 306 may be placed anywhere on the head. In particular aspects, microphones 306 are positioned at locations that minimize their sensitivity to bone-conducted sounds so long as there is a difference in the distance of acoustic path 310 for sounds originating from target source 308 to each of the microphones 306. Exemplary such locations may include locations where skin/muscle thickness is at a minimum and/or where hair covering is at a minimum.

In the illustrative embodiment described above, microphones 306 are constructed from titanium and form a part of a hermetically sealed implant housing. However, it is possible to use a satellite microphone that is positioned separate from the main implant housing via, for example, a cable. In other embodiments, it may be possible to use microphone signal(s) from a contra-laterally implanted device, where the microphone signal(s) are transmitted wirelessly or via a cable. In this way, the number of microphones used as an input to the system signal processing is not limited to two, and the signal processing used can be extrapolated to include more microphones.

FIG. 4 illustrates an exemplary noise cancellation system 440 implemented in embodiments of the present embodiment. As described below, noise cancellation system 400 comprises a pre-filtering stage 442, a roll-off compensation stage 446 and an adaptive filtering stage 444. It would be appreciated noise cancellation system 444 in accordance with embodiments of the present invention may be implemented as one or more software programs executing in a sound processor. Alternatively, noise cancellation system 444 may also be implemented in any combination of hardware, software, firmware, etc. For example, embodiments may be implemented in an application specific integrated circuit, ASIC, or other computer hardware.

In operation, air-conducted sound signals 403 are detected by microphones 206. The received sound signals are each transformed to the frequency domain by fast Fourier transform (FFT) processing, to produce electrical sound signals 242 and 244. Signals 242, 244 are used as inputs to fixed filter pre-filtering stage 442 implemented by pre-filter 230 (FIG. 2A).

As explained above with reference to FIGS. 3A-3B, the two microphones 206 are positioned such that there is a time delay for air-conducted sound 403, thereby creating a phase difference in the response between the acoustic sounds received by the two microphones. However, due to the high speed of sound conduction through bone, bone-conducted sound is presumed to arrive at the two microphones 206 with an effective path distance that is very close to zero and therefore in phase. This phase difference is sensed or otherwise detected and the noise cancellation system 440 uses the detected difference in the relative phase response between the air-conducted sound and bone-conducted sound to remove the bone-conducted sound while maintaining sufficient sensitivity to the air-conducted sound.

More particularly, noise cancellation system 440 exploits the relative phase differences by generating target reference signal 246 and a noise reference signal 254 which are adaptively filtered to eliminate the in-phase conducted sound. Target reference signal 246 and noise reference signal 254 are generated in pre-filtering stage 442.

As shown in FIG. 4, target reference signal 246 is generated through a filter subtraction method implemented by target reference generator 232. Target reference generator 232 comprises a calibrated fixed target filter 460 configured to improve the signal-to-noise ratio (SNR) over the unfiltered signals 242, 244 output by microphones 206, and a summer 262. Filter 460 is a complex frequency domain filter configured to alter both magnitude and phase of target reference signal 246.

Figure 5A:
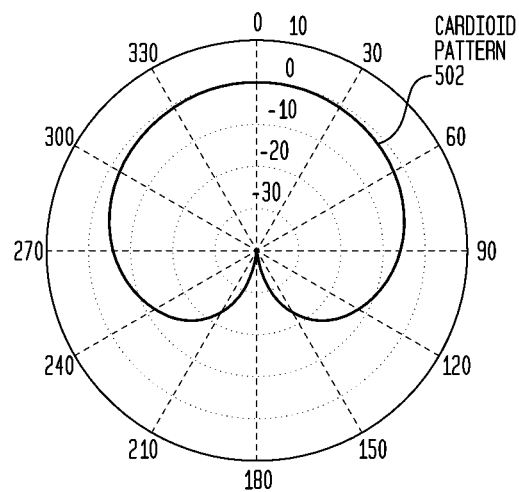
FIG. 5A illustrates a directional sensitivity pattern resulting from the implementation of a filter and subtract method.

Target reference signal 246 is a signal for presentation to the recipient, and, as such, target reference generator 232 may function as a fixed beamformer or fixed directional microphone. In traditional beamforming applications, the filter and subtract method is similar to designing a filter which creates a front facing cardioid. An exemplary front facing cardioid pattern 502 is illustrated in FIG. 5A. A cardioid pattern is a directional pattern that is more sensitive in one direction than the opposing direction. Therefore, using the configuration of FIG. 3 in which a target source 312 is at an azimuth of zero degrees, the filter and subtract method creates cardioid pattern 502 depicted in FIG. 5A which is more sensitive to the front of the recipient (anterior direction), than from the recipient's back (posterior direction). This resulting pattern assumes that unwanted sounds originate from behind the recipient.

However, generating a sensitivity shown by front facing cardioid pattern 502 suffers from several drawbacks. For example, the front facing cardioid pattern 502 will not reduce the main noise source, bone-conducted sound. Therefore, target filter 460 must be designed in such a way to reduce this dominant noise source.

Conventional filter and subtraction methods also suffer from the disadvantage of low frequency sensitivity loss, the extent of which is related to the spacing 302 of microphones 306. A large physical spacing is desirable to avoid low frequency attenuation. It is therefore important to consider not only the improvement in signal to noise ratio (SNR) with respect to spatial noise, but also the degradation in SNR with respect to the microphone noise floor.

Figure 5B:
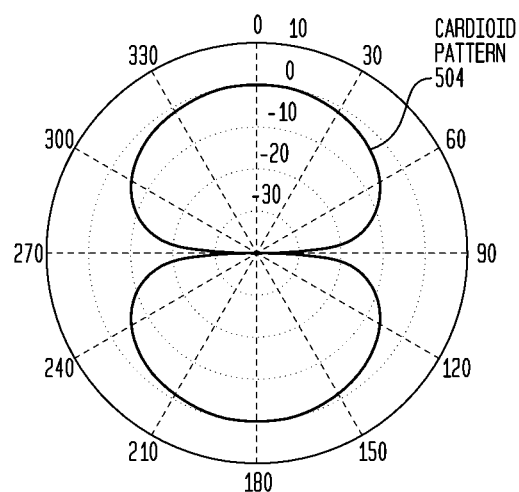
FIG. 5B illustrates a directional sensitivity pattern resulting from a filter and subtract method implemented in accordance with embodiments of the present invention.

As such, in embodiments of the present embodiment target reference generator 232 is designed to maximally cancel bone-conducted sound. FIG. 5B illustrates the theoretical directional sensitivity for a target reference signal 246 designed in accordance with embodiments of the present invention to cancel bone-conducted sound. As shown, the theoretical sensitivity is not in the shape of a typical front facing cardioid 502 (FIG. 5A), but is rather a figure eight cardioid pattern 504. Under ideal conditions in which identical microphones are presumed to detect perfectly in-phase bone-conducted sound, the filter would be unity and the resulting directional pattern of the target reference would be as shown in FIG. 5B. However, calibration of filter 460 is often utilized achieve the desired sensitivity. As discussed below with reference to FIG. 8, filter 460 is calibrated by measuring the relative response between microphones 406 in response to a bone-conducted stimulus. Designing the filter to achieve the sensitivity of FIG. 5B also reduces the low frequency sensitivity, thereby increasing the noise floor.

As shown in FIG. 4, target reference generator 232 receives electrical signals 242, 244. Electrical signal 244 from microphone 206B is filtered using filter 460. This filtering is calibrated based on the relative responses to microphones 206 to a bone-conducted stimulus. The filtered signal output by filter 460 is then subtracted from the electrical signal 242 output by microphone 206A at summer 462. This generates the target reference signal 246 from which a significant amount of received bone-conducted sound has been removed.

As noted, the pre-filtering stage 442 also creates a noise reference signal 254 which is derived from electrical sound signals 242, 244. Specifically, electrical signal 244 is provided to noise reference generator 234 and filtered by noise filter 468. Noise reference generator 234 comprises a calibrated fixed filter 468 which is a complex frequency domain filter capable of altering both magnitude and phase of signal 244. The signal output by filter 468 is then subtracted from electrical signal 242 at 470 to generate noise reference signal 254 from which the target signal has been fully or substantially removed. The resulting noise reference signal 254 is described as a back facing cardioid, i.e. a cardioid with a null at the front of the recipient (anterior direction), and having more sensitivity to the back of the recipient (posterior direction).

Figure 8:
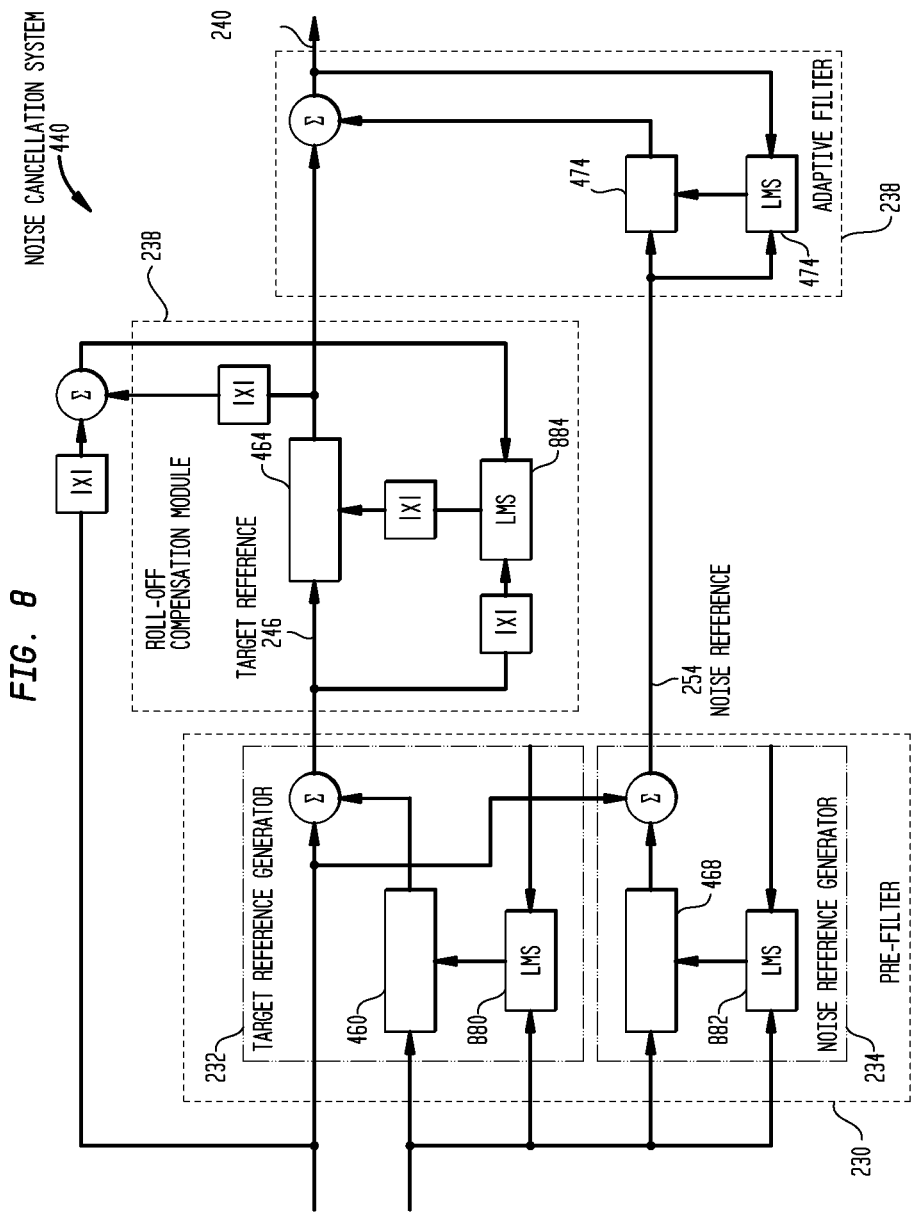
FIG. 8 illustrates the calibration of fixed filters, in accordance with embodiments of the present invention.

As described below with reference to FIG. 8, filter 468 is calibrated by presenting an acoustic stimulus from the target direction, and calculating the relative transfer function between microphones 206. Noise filter 468 applies this calculated transfer function to signal 244 via filter 468.

Figure 6A:
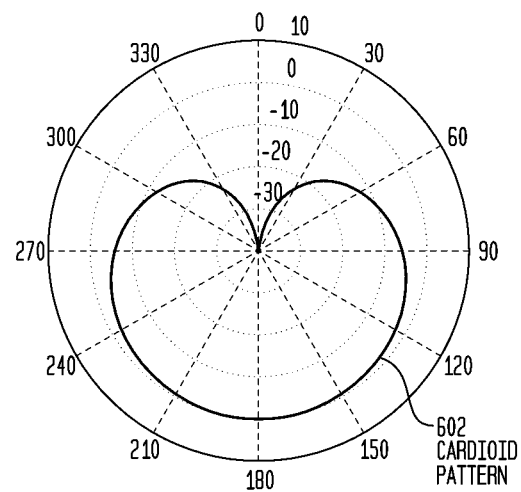
FIG. 6A illustrates a directional sensitivity pattern resulting from the implementation a noise reference generator, in accordance with embodiments of the present invention.
Figure 6B:
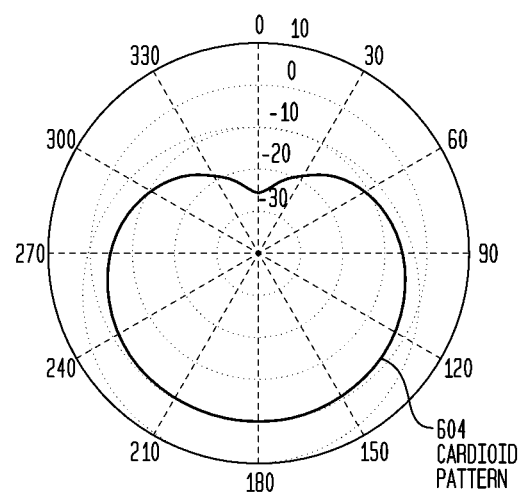
FIG. 6B illustrates a directional sensitivity pattern resulting from the implementation a noise reference generator, in accordance with embodiments of the present invention.

If noise reference signal 254 is completely free of the target signal as desired, the sensitivity will have a deep null in the direction of the target source, shown as the anterior direction in FIGS. 6A and 6B. In other words, in these embodiments noise reference signal 254 does include any sound components from the target source. This sensitivity is shown as cardioid pattern 602 in FIG. 6A. In this case, the adaptive filtering stage 444 will cause little to no distortion of the target signal while cancelling noise.

However, in practical applications noise reference signal 254 is likely to contain some target signal because the null is not sufficiently deep in the direction of the target source, and thus some components of the target source may be found in the noise reference. Such a sensitivity is shown as pattern 604 in FIG. 6B. In such embodiments, the parameters of the adaptive filtering stage 444 can be tuned to minimize target distortion while maintaining adequate noise cancellation.

As noted, target reference signal 246 is an input to roll-off compensations stage 446 implemented by roll-off compensation module 236. As is known in the art, roll-off refers to the attenuation of a signal above or below a certain frequency. Roll-off compensation module 236 applies a compensation filter 464 to target reference signal 246 to offset any roll-off that may occur in target reference signal 246. In other words, roll-off compensation module 236 is configured to ensure that the frequency shape of target reference signal 246 is the same as the unfiltered microphone signal for a sound originating from the target direction. This is accomplished through the use of filter 464 is a simple filter which is designed to alter only the magnitude of target reference signal 246 in each frequency band, thereby providing filtered target reference 248.

Figure 7:
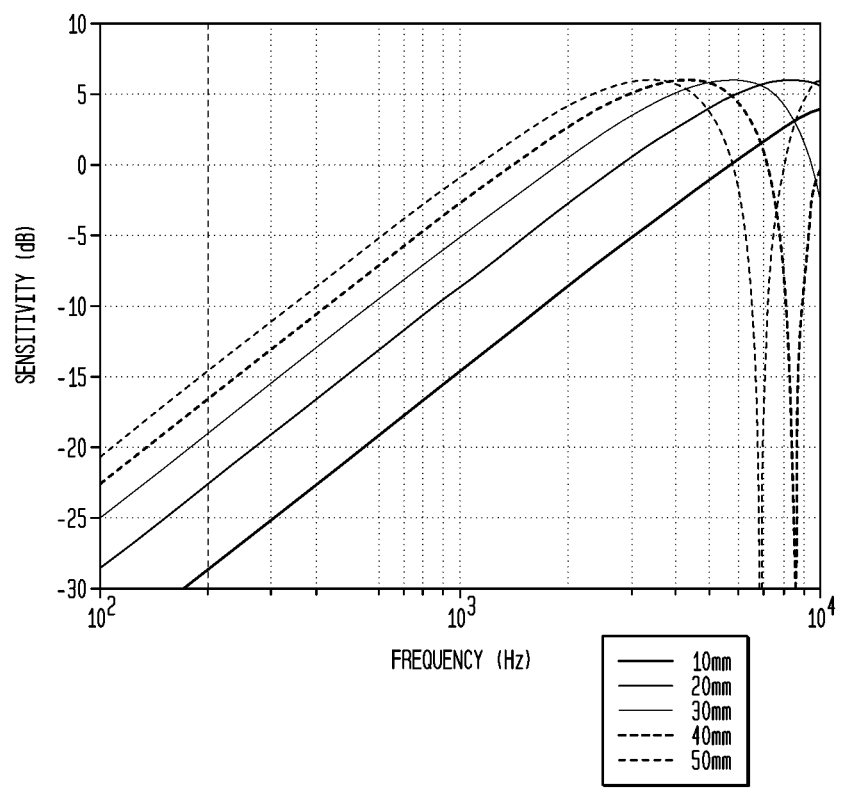
FIG. 7 illustrates the low frequency roll-off for different microphone spacing, in accordance with embodiments of the present invention.

As shown in FIG. 7, the roll-off is related to the physical distance d between microphones. Theoretical low frequency roll-off and high frequency spatial aliasing for various spacing d for a target sound source directly in front of a recipient (FIG. 3B) is shown in FIG. 7.

As shown in FIG. 7, greater spacing is better for low frequency sensitivity to air-conducted sound from a target source positioned directly in front of the recipient. However, in determining appropriate microphone spacing, low-frequency roll-off is not the only issue to consider. Specifically, while a larger spacing is generally desirable, a spacing of beyond about 50 mm causes spatial aliasing to limit the highest usable frequency to about 6 kHz. Embodiments of the present invention may make use of higher frequencies through effective mechanical isolation of microphones 206. In certain embodiments of the present invention, the largest microphone spacing that allows both microphones to fit onto the implant housing is desirable. However, alternative embodiments may separate at least one microphone from the main housing, or provide two diaphragms on the main casing and have a third microphone separate.

Embodiments of the present invention have described roll-off compensation stage 446 prior to adaptive filtering stage 444. In an alternative embodiment, roll-off compensation stage 444 occurs after adaptive filtering stage 444.

As noted, filtered target reference 248 and noise reference signal 254 are provided to adaptive filtering stage 444. Adaptive filtering stage 444 is configured to minimize the energy of an output signal 240 by removing signal components which are common to filtered target reference 248 and noise reference signal 254. That is, adaptive filter 238 is designed to remove the most dominant component common to both signals 242 and 244 which is the in-phase bone-conducted noise.

As shown in FIG. 4, adaptive filtering stage 444 comprises a sub-band Least Mean Squared (LMS) adaptive algorithm which is calibrated for use with the implanted microphones. Specifically, adaptive filtering stage 444 continually updates or adapts the coefficients of filter 472 using the normalized LMS algorithm 474 to minimize the energy of the output signal 240. The speed of adaptation of the filter coefficients may be controlled in order to increase noise cancellation or to reduce speech distortion. If the adaptive stage 230 is supplied with a good quality noise reference as discussed above, adaptive filter 472 can be set aggressively without fear of distorting the target signal. If the noise reference is degraded by the inclusion of some target signal, the adaptive stage 230 can be adjusted to minimize speech distortion at the expense of reduced noise cancellation. Details of adaptive filtering are known in the art and not discussed further herein.

In alternative embodiments, the basic LMS update procedure of adaptive filtering stage 444 can be adjusted in order to reduce target distortion introduced by the adaptive stage. The adaptation speed can be controlled to reduce target distortion, and in general slower adaptation leads to less distortion. Another potential alternative is to use a voice activity detector which halts the filter update procedure during periods of voice detection. In an implementation with more than two microphones, robustness can be improved by estimating correlation matrices for speech and noise periods independently, and used to trade off noise cancellation and speech distortion in the adaptive stage.

In further embodiments, the adaptive filtering stage may be disabled and target reference signal 246, or filtered target reference 248 is used as the system output.

In certain embodiments of the present invention, a noise cancellation system in accordance with embodiments of the present invention may comprise a sub-band implementation which is entirely implemented in the frequency domain, following a Fast Fourier transform (FFT) stage. In this way, the performance and configuration of the noise cancellation system can be defined on a frequency by frequency basis in each frequency sub-band so as to achieve maximum signal to noise ratio (SNR). The choice of configuration in each sub band can come under automatic control, or be dependent on, for example, the acoustic signal received by microphones 206, the detected sound environment, etc.

Although the above embodiment has been described in terms of a sub-band implementation, it should be appreciated a broad band time domain implementation may also be implemented with similar results.

As would be appreciated, the characteristics of implanted microphones may vary due to surgical procedure, microphone placement, microphone hardware, skin flap covering, etc. As such, in situ calibration may be necessary or desirable in order to obtain optimum performance of the noise cancellation system. Therefore, embodiments of the present invention provide for calibration of target filter 460, noise filter 468 and compensation filter 464. As described below, these filters are calibrated in situ using an acoustic stimulus or a bone-conducted stimulus.

During calibration, the noise cancellation system of the present invention implements Least Mean Squared (LMS) update blocks 880, 882 and 884 which converge the filters to desired responses. This is done by minimizing the signal output energy. Following convergence, the filter settings are then stored as the calibrated data. With the appropriate stimulus the LMS update blocks 880, 882 and 884 are enabled one at a time to perform calibration of each associated filter. All filters operate in the frequency domain on complex frequency domain FFT data. In each case, the stimulus to be used is a broad band signal so that all frequency bands can be calibrated.

To calibrate the target reference, bone-conducted sound is used as the stimulus and an LMS update 880 is used to update the target filter 460 until target reference output 246 is minimized. Calibration of filter 468 involves application of an air conducted sound from the target listening position, and an LMS update 882 is used to update filter 468 until noise reference output 254 is minimized Calibration of compensation filter 464 also involves application of an air conducted sound from the target listening. In this calibration, a target reference created using the calibrated target reference filter is further filtered by filter 464, and then compared to the unfiltered microphone signal 242 received by microphone 206A. An LMS update 884 is used to adapt the filter so the difference between the two signals is minimized. Because compensation filter 464 is a magnitude only filter, the phase of the signal is not altered. However, filter 464 operates on a complex frequency domain signal and is designed to equalize the frequency response of target reference signal 246 to the unfiltered microphone signal 242.

Although embodiments have been described with reference to calibration of each filter, it may also be possible to predict the filter requirements rather than measure them in situ. This could improve acceptance of the device since it removes the need to perform an acoustic calibration in a controlled environment. Another variation might see a combination of predicted and measured calibration of the filters.

FIG. 9A is a high level flowchart illustrating a method 900 for cancelling bone-conducted sound in a hearing prosthesis comprising at least first and second spaced implanted matched microphones. As shown, at block 902 a first implanted microphone of the hearing prosthesis receives air-conducted sound signals and bone-conducted sound signals. At block 904, a second implanted microphone of the hearing prosthesis receives the bone-conducted sound signals at substantially the same time as the first microphone. In other words, as explained above with reference to FIG. 3B, due to the high speed of sound conduction through bone, bone-conducted sound is presumed to arrive at the two microphones at substantially same time, and thus are in phase.

At block 906, the air-conducted sound signals are received, after a time delay, at the second microphone. That is, there is a time delay between receipt of the air-conducted sound signals at the first and second microphones. As detailed above with reference to FIG. 3B, this time delay causes a difference in the relative phase response between the air-conducted sound signals and bone-conducted sound signals received by the first and second microphones. At block 908, the difference in the relative phase response between the air-conducted sound signals and bone-conducted sound signals is used, as detailed elsewhere herein, to cancel the bone-conducted sound signals from a representation of the sound signals received by the first and second microphones.

FIG. 9B is a detail level flow illustrating the operations performed in block 908 of FIG. 9A to cancel the bone-conducted sound signals. At block 910, a target reference signal is generated based on the detected phase difference. The target reference signal primarily comprises the air-conducted sound signals, and the bone-conducted sound signals are substantially cancelled there from. At block 912, a noise reference signal is generated based on the detected phase difference. The noise reference signal primarily comprises the bone-conducted sound signals, and the air-conducted sound signals are substantially cancelled there from. At block 914, the target reference signal and the noise reference signal are adaptively filtered to further cancel bone-conducted sound signals from the target reference signal.

It would be appreciated by one of ordinary skill in the art that numerous variations and/or modifications may be made to the above described embodiments without departing from the spirit or scope of the invention as broadly described. For example, it is intended that the noise cancellation system will be specified on a sub-band basis so that each frequency band may be configured optimally. However, sub-bands need not all be configured in the same way.

Furthermore, in one alternative embodiment of the present invention, the configuration of the target reference may be altered. As noted above, the target filter is preferably calibrates so that it cancels at least some body noise. Under ideal conditions, this would mean that a figure eight directional pattern (FIG. 5B) results. However, an alternative is to use the unfiltered microphone signal 242, 244 as the target reference input to the adaptive filter. This may be done by setting target reference filter to zero, and the roll-off compensation filter to unity. In this way, the task of removing bone-conducted sound is then left entirely to the adaptive stage. In some situations, this can result in a more stable adaptive stage with less target distortion. Attenuation of low frequencies is avoided when creating the target reference.

As noted above, alternative embodiments of the present invention may utilize more than two microphones. The noise cancellation system is easily adaptable to n microphones, by creating n–1 noise references and using them in a multi-channel adaptive stage. The location of microphones could be anywhere on the head including on opposites sides of the head, or even elsewhere on the body, and spread across multiple implanted devices (for example binaural implanted devices) and/or components of those devices. The connection between multiple microphones could be wired or wireless. It is also possible to use a microphone that is not implanted, by combining for example an external and an implanted microphone. The underlying noise cancellation system remains conceptually the same for all of these multiple microphone situations and calibration would vary depending on the location and characteristics of the different microphones. From any given set of microphones, the most appropriate signal could be determined on a sub-band basis, and could be selected from a range of single microphone or multi-microphone processing configurations.

In an alternative embodiment, the microphones may be designed with a deliberate small difference in air-conducted sensitivity, while having matched sensitivity to bone-conducted sounds. Such an embodiment provides the ability to process signals that are received 90 degrees from a target source location. Specifically, if the air conducted sensitivities of the two microphones are the same, sounds 90 degrees from the target location arrive at the two microphones with the same amplitude and in-phase, and thus will be cancelled by the noise cancellation system as body noise. By designing in a small difference or mismatch in the air conducted sensitivity, it is possible to reduce this cancellation, which may be desirable in some sound environments. Effecting such a small mismatch between the microphones to air-conducted sounds, while still providing for substantial matching of the microphones to bone-conducted sounds, may be achieved through several different methods. In certain circumstances, this may be achieved by changing the acoustic volume of one microphone relative to the other. In other circumstances, this may be achieved by implanting identical microphones at slightly different depths such that the difference in the overlaying skin flap thickness provides the mismatch between the microphones.

Furthermore, as described above with reference to FIGS. 3A and 3B, embodiments of the present invention may be implemented with any relative position of a sound source that results in the noted time delay. Therefore, any number of target sound locations may be defined using the calibration process described above with reference to FIG. 8, and filter settings may be stored for each target direction. The filter may then be configured to use the settings that correspond to a particular source location. The selection of the appropriate settings may occur in real-time using, for example, a localization detection algorithm or may be controlled or selected by the user.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

The invention claimed is:

1. A method for cancelling bone-conducted sound during sound processing in a hearing prosthesis having first and second matched microphones implanted in a recipient in a spaced arrangement, the method comprising:

receiving, at the first microphone, air-conducted sound signals and bone-conducted sound signals substantially simultaneously;

receiving, at the second microphone, the bone-conducted sound signals at substantially the same time as the first microphone;

receiving, after a time delay, the air-conducted sound signals at the second microphone, wherein the time delay results in a relative phase difference between the air-conducted sound signals and the bone-conducted sound signals received by the second microphone; and cancelling, based on the phase difference, the bone-conducted sound signals received by the first and second microphones.

2. The method of claim 1, wherein cancelling the bone-conducted sound signals, comprises generating, based on the phase difference, a target reference signal primarily comprising the air-conducted sound signals, and from which the bone-conducted sound signals are substantially cancelled;

generating, based on the time delay, a noise reference signal primarily comprising the bone-conducted sound signals, and from which the air-conducted sound signals are substantially cancelled; and adaptively filtering the target reference signal and the noise reference signal to further cancel bone-conducted sound from the target reference signal.

3. The method of claim 2, further comprising:

filtering the generated target reference signal prior to the adaptive filtering to ensure that the frequency shape of the target reference substantially similar to the frequency shape of the received air-conducted acoustic signals.

4. The method of claim 3, wherein the filtering of the generated target reference signal comprises:

adjusting the magnitude of frequency components of the target reference signal.

5. The method of claim 2, wherein adaptively filtering the target reference signal and the noise reference signal, comprises:

removing signals components of the target reference signal and the noise reference signal which are detected in both of the target reference signal and the noise reference signal.

6. The method of claim 2, wherein generating the target reference signal, comprises filtering an output signal generated by the second microphone with a fixed target filter to generate a filtered output signal; and subtracting the filtered output signal from an output signal generated by the first microphone.

7. The method of claim 2, wherein generating the noise reference signal, comprises filtering an output signal generated by the second microphone with a fixed noise filter to generated a filtered output signal; and subtracting the filtered output signal from an output signal generated by the first microphone.

8. The method of claim 1, wherein receiving the first and second sound signals further comprises:

implementing a Fast Fourier Transform (FFT) on each of the sound signals to convert the detected signals to the frequency domain.

9. The method of claim 1, further comprising:

receiving at least a third sound signal.

10. The method of claim 2, further comprising:

calibrating one or more parameters of the adaptive filtering to minimize distortion of the air-conducted sound signals in the target reference signal, while further cancelling the bone-conducted sound signals.

11. A hearing prosthesis configured to cancel received bone-conducted sound, comprising:

first and second matched microphones configured to be implanted in a recipient in a spaced arrangement such that the first microphone receives air-conducted sound signals and bone-conducted sound signals substantially simultaneously, and wherein the second microphone receives bone-conducted sound signals at substantially the same time as the first microphone and receives the air-conducted sound signals after a time delay, the time delay resulting in a relative phase difference between the air-conducted sound signals and the bone-conducted sound signals received by the second microphone; and a noise cancellation system configured to cancel, based on the phase difference, the bone-conducted sound signals received by the first and second microphones.

12. The hearing prosthesis of claim 11, further comprising:

a target reference generator configured to generate, based on the phase difference, a target reference signal primarily comprising the air-conducted sound signals and from which the bone-conducted sound signals are substantially cancelled;

a noise reference generator configured to generate, based on the phase difference, a noise reference signal primarily comprising the bone-conducted sound signals, and from which the air-conducted sound signals are substantially cancelled; and an adaptive filter configured to utilize the target reference signal and the noise reference signal to further cancel bone-conducted sound signals from the target reference signal.

13. The hearing prosthesis of claim 12, further comprising:

a roll-off compensation module configured to filter the generated target reference signal to prior to the adaptive filtering to ensure that the frequency shape of the target reference is substantially similar to the frequency shape of the received air-conducted acoustic signals.

14. The hearing prosthesis of claim 13, wherein the roll-off compensation module adjusts the magnitude of frequency components of the target reference signal.

15. The hearing prosthesis of claim 12, wherein the adaptive filter is configured to remove signal components of the target reference signal and the noise reference signal which are detected in both of the target reference signal and the noise reference signal.

16. The hearing prosthesis of claim 12, wherein the target reference signal generator comprises:

a fixed target filter configured to filter an output signal generated by the second microphone; and a summer configured to subtract the filtered output signal from an output signal generated by the first microphone.

17. The hearing prosthesis of claim 12, wherein the noise reference signal generator comprises:

a fixed noise filter configured to filter an output signal generated by the second microphone; and a summer configured to subtract the filtered output signal from an output signal generated by the first microphone.

18. The hearing prosthesis of claim 11, wherein receiving the first and second microphones are configured to implement a Fast Fourier Transform (FFT) on each of the sound signals to convert the detected signals to the frequency domain.

19. The hearing prosthesis of claim 11, further comprising:

at least a third microphone to receive the air-conducted and bone-conducted sound signals.

20. The hearing prosthesis of claim 11, further comprising:

an implantable hermetically sealed housing, and wherein the first and second microphones are disposed on the implant housing.

* * * * *